(12) United States Patent
Shimizu et al.

(10) Patent No.: US 9,115,144 B2
(45) Date of Patent: Aug. 25, 2015

(54) FUSED HETEROCYCLIC DERIVATIVE AND PHARMACEUTICAL USE THEREOF

(75) Inventors: Kazuo Shimizu, Azumino (JP); Yusuke Onda, Azumino (JP); Masato Lizuka, Matsumoto (JP)

(73) Assignee: KISSEI PHARMACEUTICAL CO., LTD., Matsumoto-shi (JP)

( * ) Notice: Subject to any disclaimer, the term of this patent is extended or adjusted under 35 U.S.C. 154(b) by 0 days.

(21) Appl. No.: 14/240,157

(22) PCT Filed: Aug. 23, 2012

(86) PCT No.: PCT/JP2012/071330
§ 371 (c)(1),
(2), (4) Date: Apr. 3, 2014

(87) PCT Pub. No.: WO2013/027801
PCT Pub. Date: Feb. 28, 2013

(65) Prior Publication Data
US 2014/0296537 A1    Oct. 2, 2014

(30) Foreign Application Priority Data
Aug. 24, 2011  (JP) ................................. 2011-183151

(51) Int. Cl.
| C07D 495/04 | (2006.01) |
| C07D 417/14 | (2006.01) |
| C07D 277/28 | (2006.01) |
| C07D 401/14 | (2006.01) |
| C07D 333/24 | (2006.01) |
| C07D 491/048 | (2006.01) |

(52) U.S. Cl.
CPC ............ *C07D 495/04* (2013.01); *C07D 333/24* (2013.01); *C07D 491/048* (2013.01)

(58) Field of Classification Search
USPC ........ 548/453, 194; 546/276.7; 514/338, 370, 514/412
See application file for complete search history.

(56) References Cited

U.S. PATENT DOCUMENTS

| 2007/0275950 A1 | 11/2007 | Miyata et al. |
| 2009/0306396 A1 | 12/2009 | Toyoshima et al. |
| 2010/0056521 A1 | 3/2010 | Shimizu et al. |
| 2012/0015972 A1 | 1/2012 | Shimizu et al. |

FOREIGN PATENT DOCUMENTS

| CA | 2755132 A1 | 10/2010 |
| EP | 1932833 A1 | 6/2008 |
| EP | 2133332 A1 | 12/2009 |
| JP | 2000-001431 A | 1/2000 |
| WO | 2006/022374 A1 | 3/2006 |
| WO | 2007/043401 A1 | 4/2007 |
| WO | 2008/126898 A1 | 10/2008 |
| WO | 2008/126901 A1 | 10/2008 |

OTHER PUBLICATIONS

International Search Report for PCT/JP2012/071330, Mailing Date of Nov. 13, 2012.
Supplementary European Search Report dated Nov. 26, 2014, issued in corresponding EP Application No. 12825645 (2 pages).

*Primary Examiner* — Nyeemah A Grazier
(74) *Attorney, Agent, or Firm* — Westerman, Hattori, Daniels & Adrian, LLP

(57) ABSTRACT

Compounds useful as agents for the prevention or treatment of a disease associated with abnormal serum uric acid level and the like. Fused heterocyclic derivatives represented by the following formula (I) having xanthine oxidase inhibitory activities and useful as agents for the prevention or treatment of a disease associated with abnormality of serum uric acid level, or prodrugs thereof, or pharmaceutically acceptable salts thereof. In the formula (I), ring U represents $C_{6-10}$ aryl or the like; $R^1$ independently represents a hydrogen atom, a hydroxy group, $C_{1-6}$ alkyl or the like; m represents an integral number from 1 to 2; ring Q represents 5-membered heteroaryl; n represents an integral number from 1 to 3; $R^2$ independently represents a hydrogen atom, a halogen atom, $C_{1-6}$ alkyl or the like.

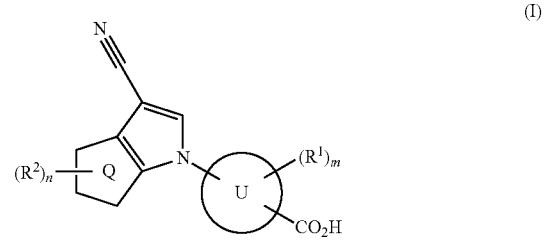

(I)

12 Claims, No Drawings

FUSED HETEROCYCLIC DERIVATIVE AND PHARMACEUTICAL USE THEREOF

TECHNICAL FIELD

The present invention relates to fused heterocyclic derivatives useful as medicaments.

More particularly, the present invention relates to fused heterocyclic derivatives having xanthine oxidase inhibitory activities and useful as agents for the prevention or treatment of a disease associated with abnormality of serum uric acid level, or prodrugs thereof, or pharmaceutically acceptable salts thereof.

BACKGROUND ART

Uric acid is the final product of purine metabolism in human. In many mammals, unlike human, uric acid is further broken down by urate oxidase (uricase) in the liver into allantoin, which is excreted through the kidney. In human, main pathway of uric acid excretion is the kidney, wherein approximately two thirds of uric acid is excreted in urine. The remaining is excreted in feces. When an excessive production or decreased excretion of uric acid occurs, that causes hyperuricemia. Hyperuricemia is classified into a uric acid overproduction type, a uric acid underexcretion type and a mixed type thereof. This classification of hyperuricemia is clinically important. Aiming for reducing adverse effects of therapeutic agents, therapeutic agents are chosen according to each class (for example, see Non-patent reference 1).

In hyperuricemia with a uric acid overproduction type, urinary excretion of uric acid increases, and when the urinary excretion of uric acid further increases by using of a uricosuric drug, the complication of urinary calculi is possibly developed. Therefore, in principle, allopurinol, a uric acid production inhibitor (or sometimes called a uric acid synthesis inhibitor, hereinafter referred to as "a uric acid production inhibitor"), is used in a uric acid overproduction type. Uric acid is produced from purine bodies, which are derived from diet and synthesized endogenously, finally by oxidizing xanthine by xanthine oxidase. Allopurinol is developed as a xanthine oxidase inhibitor and an uric acid production inhibitor used in medical practice. While allopurinol, however, is reported being effective in hyperuricemia and various diseases caused by the same, severe adverse effects such as poisoning syndrome (hypersensitivity angiitis), Stevens-Johnson syndrome, exfoliative dermatitis, aplastic anemia, liver dysfunction and the like have been also reported (for example, see Non-patent reference 2). As one of the causes, it has been pointed out that allopurinol has a nucleic acid-like structure and inhibits a pathway of pyrimidine metabolism (for example, see Non-patent reference 3).

On the other hand, in hyperuricemia with a uric acid underexcretion type, uric acid excretion decreases. It has been reported that when allopurinol, which is metabolized into oxypurinol to be excreted through the kidney by the same mechanism to uric acid, is used, the excretion of oxypurinol also decreases and that increases the incidence of liver disorders (for example, see Non-patent reference 4). Therefore, in principle, uricosuric drugs such as probenecid, benzbromarone and the like are used in a uric acid underexcretion type. These uricosuric drugs, however, also exert adverse effects such as gastrointestinal disorders, urinary calculi or the like. Particularly, benzbromarone is known as possibly causing fulminant hepatitis in the case of idiosyncratic patients (for example, see Non-patent references 5 and 6).

Thus, it is said that both of the existing uric acid production inhibitor and uricosuric drug have usage restrictions in patients or severe adverse effects. Therefore, the development of an easy-to-use agent for the treatment of hyperuricemia or the like has been desired.

Uric acid is eliminated mainly by the kidney, and the urate dynamics in the kidney has been investigated so far in some experiments using brush-border membrane vesicles (BBMV) prepared from the renal cortex (for example, see Non-patent references 7 and 8). It has been known that in human, uric acid is passed through the kidney glomerulus freely, and there are mechanisms of reabsorption and secretion of uric acid in the proximal tubule (for example, see Non-patent reference 9).

In recent years, the gene (SLC22A12) encoding the human kidney urate transporter has been identified (for example, see Non-patent reference 10). The transporter encoded by this gene (urate transporter 1, hereinafter referred to as "URAT1") is a 12-transmembrane type molecule belonging to OAT family. URAT1 mRNA was specifically expressed in the kidney, and localization of URAT1 in apical side of the proximal tubule was observed on the human kidney tissue section. In an experiment using *xenopus oocyte* expression system, uptake of uric acid through URAT1 was shown. Furthermore, it was shown that the uptake of uric acid is transported by exchange with organic anions such as lactic acid, pyrazinecarboxylic acid (PZA), nicotinic acid and the like, and the uric acid uptake through URAT1 is inhibited by uricosuric drugs, probenecid and benzbromarone. Thus, as expected by the experiment using membrane vesicles, it was strongly suggested that URAT1 is a urate/anion exchanger. That is, it was shown that URAT1 is a transporter that plays an important role in uric acid reabsorption in the kidney (for example, see Non-patent reference 10).

In addition, the relation between URAT1 and diseases became clear. Idiopathic renal hypouricemia is a disease wherein uric acid excretion is increased due to abnormal urate dynamics in the kidney and the serum uric acid level becomes low. It is known that the disease is often associated with urinary calculi or acute renal failure after exercise. URAT1 was identified as a causative gene of the renal hypouricemia (for example, see Non-patent reference 10). These things also strongly suggest that URAT1 is responsible for controlling the serum uric acid level.

Therefore, a substance having a URAT1 inhibitory activity is useful as an agent for the treatment and prevention of diseases associated with high serum uric acid levels, that is, hyperuricemia, gouty tophus, gouty arthritis, renal disorder associated with hyperuricemia, urinary calculi or the like.

In the treatment of hyperuricemia, it was reported that a combination of allopurinol of a uric acid production inhibitor and an agent having a uricosuric activity lowered the serum uric acid level more strongly than the single use of allopurinol (for example, see Non-patent references 11 and 12). Therefore, when treatment with an existing single agent can not exert effect enough, a higher therapeutic effect can be expected by a combination use of a uric acid production inhibitor and a uricosuric agent. Furthermore, for hyperuricemia with the uric acid underexcretion type, it is considered that since urinary excretion of uric acid can be decreased by lowering serum uric acid level, the risk of urinary calculi caused by the monotherapy with a uricosuric agent can be reduced. In addition, for hyperuricemia with the mixed type, high therapeutic effect is expected. Thus, an agent having both an inhibitory activity of uric acid production and a uricosuric activity is expected to become an extremely useful agent for the prevention or treatment of hyperuricemia or the like.

As a compound having both xanthine oxidase inhibitory activity and URAT1 inhibitory activity, morin, a natural product, is known (see Non-patent reference 13). In addition, biaryl or diarylether compounds are known as a compound having uricosuric action.

As compounds having xanthine oxidase inhibitory activity, for example, nitrogen-containing heterocyclic compounds (for example, see Patent reference 2), (aza)indole derivatives which are 5,6-fused heterocyclic compounds (for example, see Patent reference 3) or the like are known. However, in the references, anything is neither described nor suggested about 5,5-fused heterocyclic compounds of the present invention.

Patent reference 1: Tokkai 2000-001431 (JPA2000-001431)
Patent reference 2: International publication No. WO2007/043401 pamphlet
Patent reference 3: International publication No. WO2008/126898 pamphlet
Non-patent reference 1: Atsuo Taniguchi and 1 person, *Modern Physician*, 2004, Vol. 24, No. 8, pp. 1309-1312
Non-patent reference 2: Kazuhide Ogino and 2 persons, *Nippon Rinsho* (Japan Clinical), 2003, Vol. 61, Extra edition 1, pp. 197-201
Non-patent reference 3: Hideki Horiuchi and 6 persons, Life Science, 2000, Vol. 66, No. 21, pp. 2051-2070
Non-patent reference 4: Hisashi Yamanaka and 2 persons, *Konyosankessyo to Tsufu* (Hyperuricemia and gout), issued by Medical Review Co., 1994, Vol. 2, No. 1, pp. 103-111
Non-patent reference 5: Robert A Terkeltaub, N. Engl. J. Med., 2003, Vol. 349, pp. 1647-1655
Non-patent reference 6: Ming-Han H. Lee and 3 persons, Drug. Safety, 2008, Vol. 31, pp. 643-665
Non-patent reference 7: Francoise Roch-Ramel and 2 persons, Am. J. Physiol., 1994, Vol. 266 (Renal Fluid Electrolyte Physiol., Vol. 35), F797-F805
Non-patent reference 8: Francoise Roch-Ramel and 2 persons, J. Pharmacol. Exp. Ther., 1997, Vol. 280, pp. 839-845
Non-patent reference 9: Gim Gee Teng and 2 persons, Drugs, 2006, Vol. 66, pp. 1547-1563
Non-patent reference 10: Atsushi Enomoto and 18 persons, Nature, 2002, Vol. 417, pp. 447-452
Non-patent reference 11: S Takahashi and 5 persons, Ann. Rheum. Dis., 2003, Vol. 62, pp. 572-575
Non-patent reference 12: M. D. Feher and 4 persons, Rheumatology, 2003, Vol. 42, pp. 321-325
Non-patent reference 13: Zhifeng Yu and 2 persons, J. Pharmacol. Exp. Ther., 2006, Vol. 316, pp. 169-175

SUMMARY OF THE INVENTION

Problems to be Solved by the Invention

The problem of the present invention is to provide an agent, which has an inhibitory activity of uric acid production, for the prevention or treatment of a disease associated with abnormal serum uric acid level.

Means to Solve the Problems

The present inventors have studied earnestly to solve the above problem. As a result, it was found that fused heterocyclic derivatives represented by the following formula (I) exert an excellent xanthine oxidase inhibitory activity and extremely lower serum uric acid levels, and therefore, they can be a novel agent for the prevention or treatment of a disease associated with abnormal serum uric acid level, thereby forming the basis of the present invention.

That is, the present invention relates to:
[1] a fused heterocyclic derivative represented by the formula (I):

[Chem. 1]

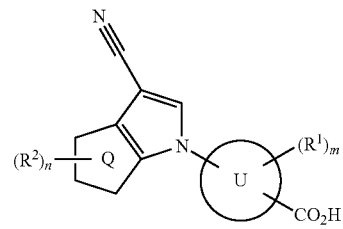

wherein
ring U represents $C_{6-10}$ aryl or 5 or 6-membered heteroaryl;
m represents an integral number from 1 to 2, and when m is 2, two $R^1$ are optionally the same or different from each other;
$R^1$ represents a hydrogen atom, a halogen atom, a hydroxy group, amino or $C_{1-6}$ alkyl which may have a fluorine atom;
ring Q represents 5-membered heteroaryl;
n represents an integral number from 1 to 3, and when n is 2 or 3, these $R^2$ are optionally the same or different from each other;
$R^2$ represents any of the following (1) to (8):
(1) a hydrogen atom;
(2) a halogen atom;
(3) a hydroxy group;
(4) amino;
(5) cyano;
(6) carboxy;
(7) carbamoyl;
(8) $C_{1-6}$ alkyl, $C_{2-6}$ alkenyl, $C_{2-6}$ alkynyl, $C_{1-6}$ alkoxy, mono or di-$C_{1-6}$ alkylamino, $C_{2-7}$ acyl, $C_{1-6}$ alkoxycarbonyl, $C_{2-7}$ acylamino, $C_{2-7}$ acyl($C_{1-6}$ alkyl)amino, mono or di-$C_{1-6}$ alkylcarbamoyl, $C_{1-6}$ alkylsulfonyl, $C_{1-6}$ alkylsulfonylamino, $C_{1-6}$ alkylsulfonyl($C_{1-6}$ alkyl)amino, mono or di-$C_{1-6}$ alkylsulfamoyl, $C_{1-6}$ alkylthio, $C_{3-8}$ cycloalkyl, 3 to 8-membered heterocycloalkyl, $C_{5-8}$ cycloalkenyl, 5 to 8-membered heterocycloalkenyl, $C_{3-8}$ cycloalkyloxy, $C_{3-8}$ cycloalkyl $C_{1-6}$ alkoxy, mono or di-$C_{3-8}$ cycloalkylamino, $C_{3-8}$ cycloalkyl($C_{1-6}$ alkyl) amino, $C_{6-10}$ aryl, 5 or 6-membered heteroaryl, $C_{6-10}$ aryloxy, $C_{6-10}$ aryl $C_{1-6}$ alkoxy, $C_{6-10}$ arylamino, $C_{6-10}$ aryl($C_{1-6}$ alkyl)amino, $C_{6-10}$ arylcarbonyl, $C_{6-10}$ arylcarbonylamino, $C_{6-10}$ arylcarbonyl($C_{1-6}$ alkyl)amino, 5 or 6-membered heteroaryloxy, 5 or 6-membered heteroaryl $C_{1-6}$ alkoxy, 5 or 6-membered heteroarylamino or 5 or 6-membered heteroaryl($C_{1-6}$ alkyl)amino each of which may independently have any group selected from substituent group A; and
substituent group A consists of a fluorine atom, a chlorine atom, a hydroxy group, amino, carboxy, carbamoyl, cyano, $C_{1-6}$ alkyl, $C_{1-6}$ alkoxy and mono or di-$C_{1-6}$ alkylamino; or a prodrug thereof, or a pharmaceutically acceptable salt thereof;
[2] a fused heterocyclic derivative as described in the above [1], wherein ring Q represents a furan ring, a pyrrole ring or a thiophene ring, or a prodrug thereof, or a pharmaceutically acceptable salt thereof;
[3] a fused heterocyclic derivative as described in the above [2], wherein the fused heterocyclic derivative represented by the formula (I) is any one of the compounds represented by the formula (Ia) to (Ic):

[Chem. 2]

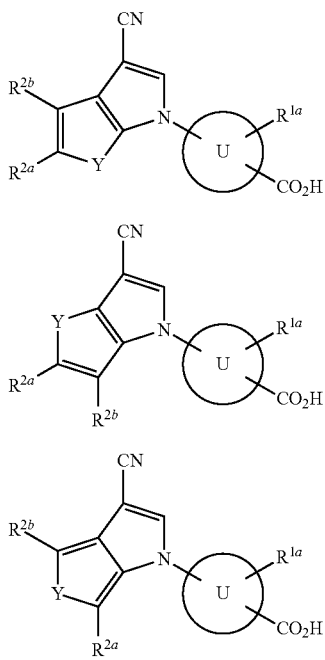

wherein

Y represents a sulfur atom or an oxygen atom;

$R^{1a}$ represents a hydrogen atom, a fluorine atom, a hydroxy group or $C_{1-6}$ alkyl;

$R^{2a}$ and $R^{2b}$ independently represent any of the following (a1) to (a3):

(a1) a hydrogen atom;

(a2) a halogen atom;

(a3) $C_{1-6}$ alkyl, $C_{1-6}$ alkoxy, mono or di-$C_{1-6}$ alkylamino, $C_{2-7}$ acyl, $C_{1-6}$ alkoxycarbonyl, mono or di-$C_{1-6}$ alkylcarbamoyl, $C_{3-8}$ cycloalkyl, 3 to 8-membered heterocycloalkyl, $C_{3-8}$ cycloalkyloxy, mono or di-$C_{3-8}$ cycloalkylamino, $C_{6-10}$ aryl or 5 or 6-membered heteroaryl each of which may have any group selected from substituent group A; and ring U and substituent group A have the same meanings as described in the above [1], or a prodrug thereof, or a pharmaceutically acceptable salt thereof;

[4] a fused heterocyclic derivative as described in the above [3], wherein Y represents a sulfur atom, or a prodrug thereof, or a pharmaceutically acceptable salt thereof;

[5] a fused heterocyclic derivative as described in any one of the above [1] to [4], wherein ring U represents a benzene ring, a pyridine ring or a thiazole ring, or a prodrug thereof, or a pharmaceutically acceptable salt thereof;

[6] a fused heterocyclic derivative as described in the above [5], wherein the group represented by the formula:

[Chem. 3]

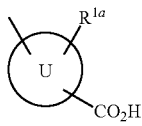

is a group represented by any of the formulas:

[Chem. 4]

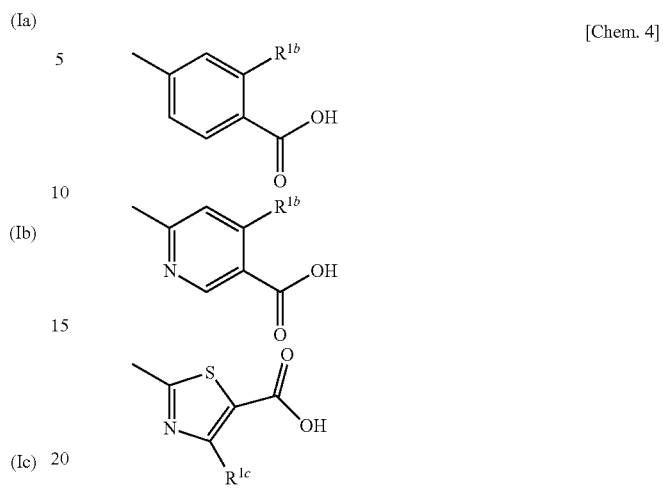

wherein $R^{1b}$ represents a hydrogen atom or a hydroxy group; and $R^{1c}$ represents a hydrogen atom or methyl; or a prodrug thereof, or a pharmaceutically acceptable salt thereof;

[7] a fused heterocyclic derivative as described in the above [6], wherein the group represented by the formula:

[Chem. 5]

is a group represented by the formula:

[Chem. 6]

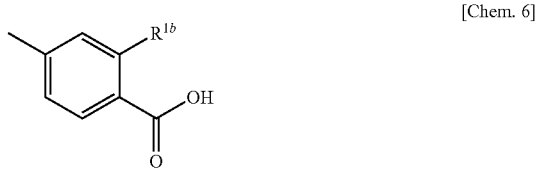

in the formula, $R^{1b}$ has the same meaning as described in the above [6], or a prodrug thereof, or a pharmaceutically acceptable salt thereof;

[8] a fused heterocyclic derivative as described in any one of the above [3] to [7], wherein $R^{2a}$ and $R^{2b}$ independently represent any of the following (b1) to (b3):

(b1) a hydrogen atom;

(b2) a halogen atom;

(b3) $C_{1-6}$ alkyl, $C_{1-6}$ alkoxy, mono or di-$C_{1-6}$ alkylamino, $C_{1-6}$ alkoxycarbonyl, mono or di-$C_{1-6}$ alkylcarbamoyl, $C_{3-8}$ cycloalkyl, 3 to 8-membered heterocycloalkyl, $C_{6-10}$ aryl or 5 or 6-membered heteroaryl each of which may have a fluorine atom; or a prodrug thereof, or a pharmaceutically acceptable salt thereof;

[9] a fused heterocyclic derivative as described in the above [8], wherein $R^{2a}$ and $R^{2b}$ independently represent a hydrogen atom, a halogen atom or $C_{1-6}$ alkyl which may have a fluorine atom, or a prodrug thereof, or a pharmaceutically acceptable salt thereof;

[10] a fused heterocyclic derivative as described in the above [9], wherein $R^{1a}$ or $R^{1b}$ represents a hydroxy group with the proviso that the term "$R^{1a}$ or $R^{1b}$ represents a hydroxy group" means that $R^{1a}$ is a hydroxy group when $R^{1a}$ is used in a definition, or $R^{1b}$ is a hydroxy group when $R^{1b}$ is used in a definition; and $R^{2a}$ and $R^{2b}$ independently represent a hydrogen atom or methyl, or a prodrug thereof, or a pharmaceutically acceptable salt thereof;

[11] a pharmaceutical composition comprising as an active ingredient a fused heterocyclic derivative as described in any one of the above [1] to [10], or a prodrug thereof, or a pharmaceutically acceptable salt thereof;

[12] a pharmaceutical composition as described in the above [11], for use in the prevention or treatment of a disease selected from the group consisting of hyperuricemia, gouty tophus, gouty arthritis, renal disorder associated with hyperuricemia and urinary calculi;

[13] a pharmaceutical composition as described in the above [12], for use in the prevention or treatment of hyperuricemia;

[14] a pharmaceutical composition as described in the above [12], which is an agent for lowering serum uric acid level;

[15] a pharmaceutical composition as claimed in the above [12], which is a uric acid production inhibitor; [16] a xanthine oxidase inhibitor comprising as an active ingredient a fused heterocyclic derivative as described in any one of the above [1] to [10], or a prodrug thereof, or a pharmaceutically acceptable salt thereof; and the like.

In the present invention, each term has the following meaning unless otherwise specified.

The term "$C_{1-6}$ alkyl" means a straight-chained or a branched alkyl group having 1 to 6 carbon atoms, and for example, methyl, ethyl, propyl, isopropyl, butyl, isobutyl, sec-butyl, tert-butyl and the like can be illustrated.

The term "$C_{2-6}$ alkenyl" means a straight-chained or a branched alkenyl group having 2 to 6 carbon atoms, and for example, vinyl, allyl, 1-propenyl and the like can be illustrated.

The term "$C_{2-6}$ alkynyl" means a straight-chained or a branched alkynyl group having 2 to 6 carbon atoms, and for example, ethynyl, 2-propynyl and the like can be illustrated.

The term "$C_{1-6}$ alkoxy" means a straight-chained or a branched alkoxy group having 1 to 6 carbon atoms, and methoxy, ethoxy, propoxy, isopropoxy and the like can be illustrated.

The term "mono or di-$C_{1-6}$ alkylamino" means an amino group mono- or di-substituted by the above $C_{1-6}$ alkyl.

The term "$C_{2-7}$ acyl" means a group represented by ($C_{1-6}$ alkyl)-C(O)—, and acetyl, propionyl and the like can be illustrated.

The term "$C_{1-6}$ alkoxycarbonyl" means a group represented by ($C_{1-6}$ alkoxy)-C(O)—, and methoxycarbonyl, ethoxycarbonyl and the like can be illustrated.

The term "$C_{2-7}$ acylamino" means a group represented by ($C_{1-6}$ alkyl)-C(O)NH—.

The term "$C_{2-7}$ acyl($C_{1-6}$ alkyl)amino" means an amino group substituted by the above $C_{2-7}$ acyl and the above $C_{1-6}$ alkyl.

The term "mono or di-$C_{1-6}$ alkylcarbamoyl" means a carbamoyl group mono- or di-substituted by the above $C_{1-6}$ alkyl.

The term "$C_{1-6}$ alkylsulfonyl" means a group represented by ($C_{1-6}$ alkyl)-$SO_2$—, and methanesulfonyl, ethanesulfonyl, propanesulfonyl, butanesulfonyl and the like can be illustrated.

The term "$C_{1-6}$ alkylsulfonylamino" means a group represented by ($C_{1-6}$ alkyl)-$SO_2$—NH—, and methanesulfonylamino, ethanesulfonylamino, propanesulfonylamino, butanesulfonylamino and the like can be illustrated.

The term "$C_{1-6}$ alkylsulfonyl($C_{1-6}$ alkyl)amino" means an amino group substituted by the above $C_{1-6}$ alkylsulfonyl and the above $C_{1-6}$ alkyl.

The term "mono or di-$C_{1-6}$ alkylsulfamoyl" means a sulfamoyl group mono- or di-substituted by the above $C_{1-6}$ alkyl.

The term "$C_{1-6}$ alkylthio" means a straight-chained or a branched alkylthio group having 1 to 6 carbon atoms, and methylthio, ethylthio and the like can be illustrated.

The term "$C_{3-8}$ cycloalkyl" means a 3 to 8-membered saturated cyclic hydrocarbon group, and cyclopropyl, cyclobutyl, cyclopentyl, cyclohexyl, cycloheptyl, cyclooctyl and the like can be illustrated.

The term "3 to 8-membered heterocycloalkyl" means a 3 to 8-membered heterocycloalkyl group having 1 or 2 hetero atoms selected from an oxygen atom, a sulfur atom and a nitrogen atom in the ring, and 2-pyrrolidinyl, 4-piperidyl, 2-tetrahydrofuryl, 4-tetrahydropyranyl and the like can be illustrated.

The term "$C_{5-8}$ cycloalkenyl" means a 5 to 8-membered cycloalkenyl group, and cyclopentenyl, cyclohexenyl and the like can be illustrated.

The term "5 to 8-membered heterocycloalkenyl" means a 5 to 8-membered heterocycloalkenyl group having 1 or 2 hetero atoms selected from an oxygen atom, a sulfur atom and a nitrogen atom in the ring, and 2,3-dihydrofuryl, 2,5-dihydrofuryl, 3,4-dihydro-2H-pyranyl and the like can be illustrated.

The term "$C_{3-8}$ cycloalkyloxy" means a group represented by ($C_{3-8}$ cycloalkyl)-O—, and cyclopropyloxy, cyclobutyloxy, cyclohexyloxy and the like can be illustrated.

The term "$C_{3-8}$ cycloalkyl $C_{1-6}$ alkoxy" means the above $C_{1-6}$ alkoxy group substituted by the above $C_{3-8}$ cycloalkyl.

The term "mono or di-$C_{3-8}$ cycloalkylamino" means an amino group mono- or di-substituted by the above $C_{3-8}$ cycloalkyl.

The term "$C_{3-8}$ cycloalkyl($C_{1-6}$ alkyl)amino" means an amino group substituted by the above $C_{3-8}$ cycloalkyl and the above $C_{1-6}$ alkyl.

The term "$C_{6-10}$ aryl" means phenyl or naphthyl.

The term "5 or 6-membered heteroaryl" means a 5 or 6-membered aromatic heterocyclic group having any 1 to 4 hetero atoms selected from an oxygen atom, a sulfur atom and a nitrogen atom in the ring, and thiazolyl, oxazolyl, isothiazolyl, isoxazolyl, pyridyl, pyrimidyl, pyrazinyl, pyridazinyl, pyrrolyl, furyl, thienyl, imidazolyl, pyrazolyl, 1,3,4-oxadiazolyl, 1,3,4-thiadiazolyl, 1,2,3-triazolyl, tetrazolyl, furazanyl and the like can be illustrated.

The term "5-membered heteroaryl" means a 5-membered aromatic heterocyclic group having any 1 to 3 hetero atoms selected from an oxygen atom, a sulfur atom and a nitrogen atom in the ring, and furan, thiophene, pyrrole, oxazole, isoxazole, thiazole, isothiazole, imidazole, pyrazole, triazole and the like can be illustrated.

The term "$C_{6-10}$ aryloxy" means a group represented by ($C_{6-10}$ aryl)-O—, and phenyloxy and the like can be illustrated.

The term "$C_{6-10}$ aryl $C_{1-6}$ alkoxy" means the above $C_{1-6}$ alkoxy group substituted by the above $C_{6-10}$ aryl.

The term "$C_{6-10}$ arylamino" means a group represented by ($C_{6-10}$ aryl)-NH—.

The term "$C_{6-10}$ aryl($C_{1-6}$ alkyl)amino" means an amino group substituted by the above $C_{6-10}$ aryl and the above $C_{1-6}$ alkyl.

The term "$C_{6-10}$ arylcarbonyl" means a group represented by ($C_{6-10}$ aryl)-C(O)—, and benzoyl group and the like can be illustrated.

The term "$C_{6-10}$ arylcarbonylamino" means a group represented by ($C_{6-10}$ aryl)-C(O)NH—.

The term "$C_{6-10}$ arylcarbonyl($C_{1-6}$ alkyl)amino" means an amino group substituted by the above $C_{6-10}$ arylcarbonyl and the above $C_{1-6}$ alkyl.

The term "5 or 6-membered heteroaryloxy" means a group represented by (5 or 6-membered heteroaryl)-O—.

The term "5 or 6-membered heteroaryl $C_{1-6}$ alkoxy" means a $C_{1-6}$ alkoxy group substituted by the above 5 or 6-membered heteroaryl.

The term "5 or 6-membered heteroarylamino" means a group represented by (5 or 6-membered heteroaryl)-NH—.

The term "5 or 6-membered heteroaryl($C_{1-6}$ alkyl)amino" means an amino group substituted by the above 5 or 6-membered heteroaryl and the above $C_{1-6}$ alkyl.

The term "halogen atom" means a fluorine atom, a chlorine atom, a bromine atom or an iodine atom.

The term "$C_{1-6}$ alkylene" means a divalent group derived from the above $C_{1-6}$ alkyl.

The term "may have a fluorine atom" means optionally having 1 to 5 fluorine atoms as substituent. In addition, when the group which may have a fluorine atom is methyl, methoxy or N-methylamino, it means optionally having 1 to 3 fluorine atoms.

The term "may have any group selected from substituent group A" means optionally having 1 to 3 same or different groups selected from substituent group A, and having none or 1 substituent is preferred. With the proviso that when the group selected from substituent group A is a fluorine atom, it has the same meaning of the above "may have a fluorine atom".

A fused heterocyclic derivative represented by the formula (I) of the present invention can be also prepared, for example, by a method described in the following example or a similar method thereto, or a method described in literatures or a similar method thereto and the like. In addition, when a protective group is necessary, operations of introduction and deprotection can be also conducted optionally in combination according to a general method (for example, Protective Groups in Organic Synthesis (the forth edition)). Heating in each reaction can be also optionally conducted by using microwave irradiation.

As the protective groups used in the present invention, various protective groups generally used in organic synthesis reaction can be used. For example, as the protective groups of a hydroxy group, in addition to a p-methoxybenzyl group, a benzyl group, a methoxymethyl group, an acetyl group, a pivaloyl group, a benzoyl group, a tert-butyldimethylsilyl group, a tert-butyldiphenylsilyl group, an allyl group and the like, when two hydroxy groups are adjacent, an isopropylidene group, a cyclopentylidene group, a cyclohexylidene group and the like can be illustrated. As the protective groups of a thiol group, a p-methoxybenzyl group, a benzyl group, an acetyl group, a pivaloyl group, a benzoyl group, a benzyloxycarbonyl group and the like can be illustrated. As the protective groups of an amino group, a benzyloxycarbonyl group, a tert-butoxycarbonyl group, a benzyl group, a p-methoxybenzyl group, a trifluoroacetyl group, an acetyl group, a phthaloyl group and the like can be illustrated. As the protective groups of a carboxy group, a $C_{1-6}$ alkyl group, a benzyl group, a tert-butyldimethylsilyl group, an allyl group and the like can be illustrated.

A compound represented by the formula (I) of the present invention can be isolated or purified by conventional isolation techniques, such as fractional recrystallization, purification by chromatography, solvent extraction, solid-phase extraction and the like.

A fused heterocyclic derivative represented by the formula (I) of the present invention can be converted into pharmaceutically acceptable salts thereof in the usual way. As such a salt, an acid additive salt with a mineral acid such as hydrochloric acid, hydrobromic acid, hydroiodic acid, sulfuric acid, nitric acid, phosphoric acid and the like, an acid additive salt with an organic acid such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, benzoic acid, glutamic acid, aspartic acid and the like, a salt with an inorganic base such as a sodium salt, a potassium salt, a calcium salt, a magnesium salt, a zinc salt, a lithium salt, an aluminum salt and the like, an additive salt with an organic base such as N-methyl-D-glucamine, N,N'-dibenzylethylenediamine, 2-aminoethanol, tris(hydroxymethyl)aminomethane, arginine, lysine, piperazine, choline, diethylamine, 4-phenylcyclohexylamine and the like can be illustrated.

Among the fused heterocyclic derivatives represented by the formula (I) of the present invention, in a compound having a chiral carbon atom, there are a compound of R configuration and a compound of S configuration for each chiral carbon. In the present invention, either of the optical isomers can be employed, and a mixture of the optical isomers thereof can be also employed.

In a fused heterocyclic derivative represented by the formula (I) of the present invention, there can be some tautomers, and the compounds of the present invention also include these tautomers.

In the present invention, the term "prodrug" means a compound to be converted into a compound represented by the formula (I) within an organism. A prodrug of a compound represented by the formula (I) of the present invention can be prepared by introducing an appropriate group forming a prodrug into any one or more groups selected from a hydroxy group, an amino group, a carboxy group and other groups which can form a prodrug of the compound represented by the formula (I) using a corresponding reagent to produce a prodrug such as a halide compound or the like in the usual way, and then by suitably isolating and purifying in the usual way as occasion demands. See *Gekkan-Yakuji iyakuhin tekiseisiyou no tameno rinsyou yakubutsudoutai* (monthly pharmaceutical, clinical pharmacokinetics for the proper use of pharmaceutical products), March 2000 extra edition, Vol. 42, No. 4, pp. 669-707, and *New Drug Delivery System*, published by CMC Co., Ltd., 2000 Jan. 31., pp. 67-173.

In the present invention, a prodrug is preferably a compound having a group forming a prodrug in a hydroxy group or a carboxy group, and more preferably a compound having a group forming a prodrug in a carboxy group.

As a group forming a prodrug used in an amino group, for example, $C_{1-6}$ alkyl-CO— such as acetyl, propionyl, butyryl, isobutyryl, pivaloyl and the like; $C_{6-10}$ aryl-CO— such as benzoyl and the like; $C_{1-6}$ alkyl-O—$C_{1-6}$ alkylene-CO—; $C_{1-6}$ alkyl-OCO—$C_{1-6}$ alkylene-CO—; $C_{1-6}$ alkyl-OCO— such as methyloxycarbonyl, ethyloxycarbonyl, propyloxycarbonyl, isopropyloxycarbonyl, tert-butyloxycarbonyl and the like; $C_{1-6}$ alkyl-O—$C_{1-6}$ alkylene-OCO—; $C_{1-6}$ alkyl-COO—$C_{1-6}$ alkylene such as acetyloxymethyl, pivaloyloxymethyl, 1-(acetyloxy)ethyl, 1-(pivaloyloxy)ethyl and the like; $C_{1-6}$ alkyl-OCOO—$C_{1-6}$ alkylene such as methyloxycarbonyloxymethyl, 1-(methyloxycarbonyloxy)ethyl, ethyloxycarbonyloxymethyl, 1-(ethyloxycarbonyloxy)ethyl, isopropyloxycarbonyloxymethyl, 1-(isopropyloxycarbonyloxy)ethyl, tert-butyloxycarbonyloxymethyl, 1-(tert-butyloxycarbonyloxy)ethyl and the like; $C_{3-8}$ cycloalkyl-OCOO—$C_{1-6}$ alkylene such as cyclohexyloxycarbonyloxymethyl, 1-(cyclohexyloxycarbonyloxy)ethyl and the like; an ester or an amide with an amino acid such as glycine and the like; and the like can be illustrated.

As a group forming a prodrug used in a hydroxy group, a group forming a prodrug used in the above amino group can be illustrated, it is preferably $C_{1-6}$ alkyl-CO—; $C_{1-6}$ alkyl-OCOO—$C_{1-6}$ alkylene; or $C_{3-8}$ cycloalkyl-OCOO—$C_{1-6}$ alkylene, and more preferably acetyl, 1-(methyloxycarbonyloxy)ethyl, ethyloxycarbonyloxymethyl, 1-(ethyloxycarbonyloxy)ethyl, 1-(isopropyloxycarbonyloxy)ethyl or 1-(cyclohexyloxycarbonyloxy)ethyl.

As a group forming a prodrug used in a carboxy group, for example, $C_{1-6}$ alkyl such as methyl, ethyl, propyl, isopropyl, butyl, tert-butyl and the like; $C_{1-6}$ alkyl-COO—$C_{1-6}$ alkylene such as pivaloyloxymethyl, acetyloxymethyl, 1-(pivaloyloxy)ethyl, 1-(acetyloxy)ethyl and the like; $C_{1-6}$ alkyl-OCOO—$C_{1-6}$ alkylene such as methyloxycarbonyloxymethyl, 1-(methyloxycarbonyloxy)ethyl, ethyloxycarbonyloxymethyl, 1-(ethyloxycarbonyloxy)ethyl, isopropyloxycarbonyloxymethyl, 1-(isopropyloxycarbonyloxy)ethyl, tert-butyloxycarbonyloxymethyl, 1-(tert-butyloxycarbonyloxy)ethyl and the like; $C_{3-8}$ cycloalkyl-OCOO—$C_{1-6}$ alkylene such as cyclohexyloxycarbonyloxymethyl, 1-(cyclohexyloxycarbonyloxy)ethyl; 2-hydroxyethyl; 2-(dimethylamino)ethyl; 2-amino-2-methoxycarbonylethyl and the like can be illustrated, it is preferably $C_{1-6}$ alkyl, $C_{1-6}$ alkyl-OCOO—$C_{1-6}$ alkylene or $C_{3-8}$ cycloalkyl-OCOO—$C_{1-6}$ alkylene, and more preferably methyl, ethyl, propyl, isopropyl, butyl, 1-(methyloxycarbonyloxy)ethyl, 1-(ethyloxycarbonyloxy)ethyl, 1-(isopropyloxycarbonyloxy)ethyl or 1-(cyclohexyloxycarbonyloxy)ethyl.

In the present invention, a pharmaceutically acceptable salt also includes a solvate thereof with a pharmaceutically acceptable solvent such as water, ethanol or the like.

A pharmaceutical composition of the present invention is useful for the prevention or treatment of diseases associated with high serum uric acid levels such as hyperuricemia, gouty tophus, gouty arthritis, renal disorder associated with hyperuricemia, urinary calculi or the like, especially for hyperuricemia.

When the pharmaceutical composition of the present invention are employed in the practical prevention or treatment, the dosage of a compound represented by the formula (I) or a prodrug thereof or a pharmaceutically acceptable salt thereof as an active ingredient is appropriately decided depending on the age, sex, body weight, degree of disorders and treatment of each patient and the like, for example, which is approximately within the range of from 1 to 2000 mg per day, more preferably the range of from 10 to 200 mg per day, per adult human in the case of oral administration, and approximately within the range of from 0.5 to 1000 mg per day, more preferably the range of from 5 to 100 mg per day, per adult human in the case of parenteral administration, and the daily dose can be divided into one to several doses per day and administered.

When a pharmaceutical composition of the present invention are employed in the practical prevention or treatment, various dosage forms are orally or parenterally used depending on their uses, for example, formulations for oral administration such as powders, fine granules, granules, tablets, capsules, dry syrups or the like are preferable.

These pharmaceutical compositions can be prepared depending on their formulations optionally by admixing an appropriate pharmaceutical additive such as excipients, disintegrators, binders, lubricants and the like in accordance with conventional pharmaceutical methods.

For example, powders can be formulated by, if desired, admixing well an active ingredient with appropriate excipients, lubricants and the like. For example, tablets can be formulated by tableting an active ingredient with appropriate excipients, disintegrators, binders, lubricants and the like in accordance with conventional methods, further if desired, can be suitably coated to provide film-coated tablets, sugar-coated tablets, enteric-coated tablets and the like. For example, capsules can be formulated by admixing well an active ingredient with appropriate excipients, lubricants and the like, or formulating fine granules or granules in accordance with conventional methods, and filling it in appropriate capsules. Furthermore, in the case of such an oral administration drug, it can be also formulated by conducting quick-release or sustained-release formulation depending on the prevention or the treatment methods.

A compound represented by the formula (I) of the present invention or a prodrug thereof, or a pharmaceutically acceptable salt thereof can be also used in combination with any other drug for the treatment of hyperuricemia or drug for the treatment of gout. As any other drug for the treatment of hyperuricemia used in the present invention, for example, urinary alkalizers such as sodium hydrogen carbonate, potassium citrate, sodium citrate and the like, and the like can be also illustrated. In addition, as any other drug for the treatment of gout, colchicine, or non-steroidal anti-inflammatory drugs such as indomethacin, naproxen, fenbufen, pranoprofen, oxaprozin, ketoprofen, etoricoxib, tenoxicam and the like and steroids and the like can be also illustrated. When used in combination with any other drug for the treatment of hyperuricemia or drug for the treatment of gout, not only a single pharmaceutical composition comprising together with the active ingredient of the present invention and the other active ingredient can be used but also pharmaceutical compositions which separately contain each active ingredient may be used for simultaneous administration or administration at different dosage intervals. Furthermore, when used in combination with any other drug than the active ingredient of the present invention, the dosage of the compound of the present invention can be reduced depending on the dosage of the other drug used in combination, as the case may be, an advantageous effect more than an additive effect in the prevention or treatment of the above diseases can be obtained, or an adverse effect of the other drug used in combination can be avoided or declined.

As one of the embodiments in the present invention, a preferred embodiment in the fused heterocyclic derivatives represented by the formula (I) is illustrated below. It is independent or may be optionally combine, respectively.

Ring Q is preferably a furan ring, a pyrrole ring or a thiophene ring, more preferably a furan ring or a thiophene ring, and even more preferably a thiophene ring.

A fused heterocyclic derivative represented by the formula (I) is preferably a compound represented by the above formula (Ia) to (Ic).

Ring U is preferably a benzene ring, a pyridine ring or a thiazole ring, more preferably a benzene ring or a pyridine ring, and even more preferably a benzene ring.

$R^1$ is preferably independently a hydrogen atom, a fluorine atom, a hydroxy group or $C_{1-6}$ alkyl, and more preferably a hydrogen atom, a hydroxy group or methyl.

$R^2$ is any of the following (1) to (8):
(1) a hydrogen atom;
(2) a halogen atom;
(3) a hydroxy group;
(4) amino;
(5) cyano;
(6) carboxy;
(7) carbamoyl;
(8) $C_{1-6}$ alkyl, $C_{2-6}$ alkenyl, $C_{2-6}$ alkynyl, $C_{1-6}$ alkoxy, mono or di-$C_{1-6}$ alkylamino, $C_{2-7}$ acyl, $C_{1-6}$ alkoxycarbonyl, $C_{2-7}$ acylamino, $C_{2-7}$ acyl($C_{1-6}$ alkyl)amino, mono or di-$C_{1-6}$ alkylcarbamoyl, $C_{1-6}$ alkylsulfonyl, $C_{1-6}$ alkylsulfonylamino, $C_{1-6}$ alkylsulfonyl($C_{1-6}$ alkyl)amino, mono or di-$C_{1-6}$ alkylsulfamoyl, $C_{1-6}$ alkylthio, $C_{3-8}$ cycloalkyl, 3 to 8-membered heterocycloalkyl, $C_{5-8}$ cycloalkenyl, 5 to 8-membered heterocycloalkenyl, $C_{3-8}$ cycloalkyloxy, $C_{3-8}$ cycloalkyl $C_{1-6}$ alkoxy, mono or di-$C_{3-8}$ cycloalkylamino, $C_{3-8}$ cycloalkyl($C_{1-6}$ alkyl) amino, $C_{6-10}$ aryl, 5 or 6-membered heteroaryl, $C_{6-10}$ aryloxy, $C_{6-10}$ aryl $C_{1-6}$ alkoxy, $C_{6-10}$ arylamino, $C_{6-10}$ aryl($C_{1-6}$ alkyl)amino, $C_{6-10}$ arylcarbonyl, $C_{6-10}$ arylcarbonylamino, $C_{6-10}$ arylcarbonyl($C_{1-6}$ alkyl)amino, 5 or 6-membered heteroaryloxy, 5 or 6-membered heteroaryl $C_{1-6}$ alkoxy, 5 or 6-membered heteroarylamino or 5 or 6-membered heteroaryl($C_{1-6}$ alkyl)amino each of which may independently have any group selected from the above substituent group A;

preferably independently any of the following (a1) to (a3):
(a1) a hydrogen atom;
(a2) a halogen atom;
(a3) $C_{1-6}$ alkyl, $C_{1-6}$ alkoxy, mono or di-$C_{1-6}$ alkylamino, $C_{2-7}$ acyl, $C_{1-6}$ alkoxycarbonyl, mono or di-$C_{1-6}$ alkylcarbamoyl, $C_{3-8}$ cycloalkyl, 3 to 8-membered heterocycloalkyl, $C_{3-8}$ cycloalkyloxy, mono or di-$C_{3-8}$ cycloalkylamino, $C_{6-10}$ aryl or 5 or 6-membered heteroaryl each of which may have any group selected from the above substituent group A;

more preferably independently any of the following (b1) to (b3):
(b1) a hydrogen atom;
(b2) a halogen atom;
(b3) $C_{1-6}$ alkyl, $C_{1-6}$ alkoxy, mono or di-$C_{1-6}$ alkylamino, $C_{1-6}$ alkoxycarbonyl, mono or di-$C_{1-6}$ alkylcarbamoyl, $C_{3-8}$ cycloalkyl, 3 to 8-membered heterocycloalkyl, $C_{6-10}$ aryl or 5 or 6-membered heteroaryl each of which may have a fluorine atom;

even more preferably independently a hydrogen atom, a halogen atom, or $C_{1-6}$ alkyl which may have a fluorine atom;
even more preferably independently a hydrogen atom or $C_{1-6}$ alkyl; and
even more preferably a hydrogen atom or methyl.

With the proviso that when $R^2$ binds to a nitrogen atom in ring Q, $R^2$ is any of the following groups: $C_{1-6}$ alkyl, $C_{2-6}$ alkenyl, $C_{2-7}$ acyl, $C_{1-6}$ alkoxycarbonyl, $C_{1-6}$ alkylsulfonyl, $C_{3-8}$ cycloalkyl, 3 to 8-membered heterocycloalkyl, $C_{5-8}$ cycloalkenyl, 5 to 8-membered heterocycloalkenyl, $C_{6-10}$ aryl, 5 or 6-membered heteroaryl and $C_{6-10}$ arylcarbonyl.

As one of the embodiments in the present invention, the fused heterocyclic derivative represented by the formula (I) is a compound represented by the following general formula (IIa).

The general formula (IIa):

[Chem. 7]

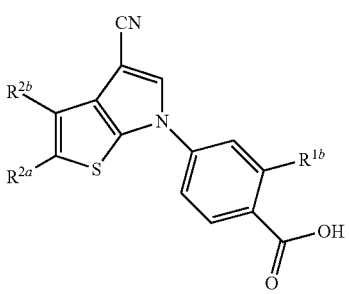

(IIa)

wherein, preferably, $R^{1b}$ is a hydrogen atom or a hydroxy group, and $R^{2a}$ and $R^{2b}$ are independently a hydrogen atom, a halogen atom or $C_{1-6}$ alkyl which may have a fluorine atom; and
more preferably, $R^{1b}$ is a hydroxy group, and $R^{2a}$ and $R^{2b}$ are independently a hydrogen atom or methyl.

As one of the embodiments in the present invention, the fused heterocyclic derivative represented by the formula (I) is a compound represented by the following general formula (IIb).

The general formula (IIb):

[Chem. 8]

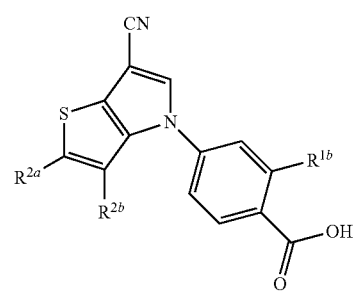

(IIb)

wherein, preferably, $R^{1b}$ is a hydrogen atom or a hydroxy group, and $R^{2a}$ and $R^{2b}$ are independently a hydrogen atom, a halogen atom or $C_{1-6}$ alkyl which may have a fluorine atom; and
more preferably, $R^{1b}$ is a hydroxy group, and $R^{2a}$ and $R^{2b}$ are independently a hydrogen atom or methyl.

As one of the embodiments in the present invention, the fused heterocyclic derivative represented by the formula (I) is a compound represented by the following general formula (IIc).

The general formula (IIc):

[Chem. 9]

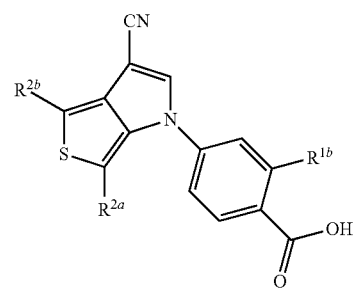

(IIc)

wherein, preferably, $R^{1b}$ is a hydrogen atom or a hydroxy group, and $R^{2a}$ and $R^{2b}$ are independently a hydrogen atom, a halogen atom or $C_{1-6}$ alkyl which may have a fluorine atom; and
more preferably, $R^{1b}$ is a hydroxy group, and $R^{2a}$ and $R^{2b}$ are independently a hydrogen atom or methyl.

As another embodiment in the present invention, (i) when ring U is a benzene ring, in $(R^1)_m$, preferably, m is 1 and $R^1$ is a hydroxy group, or m is 2, one of $R^1$ is a hydroxy group, and the other of $R^1$ is a halogen atom, and more preferably, m is 1 and $R^1$ is a hydroxy group; and (ii) when ring U is a thiazole ring, in $(R^1)_m$, preferably, m is 1 and $R^1$ is a hydrogen atom or methyl.

Independently of this or in addition to this, in $(R^2)_m$, preferably, n is 1 and $R^2$ is a hydrogen atom, a halogen atom or $C_{1-6}$ alkyl, or n is 2, one of $R^2$ is $C_{1-6}$ alkyl, and the other of $R^2$ is a hydrogen atom or a halogen atom, more preferably, n is 1 and $R^2$ is a hydrogen atom, a halogen atom or $C_{1-6}$ alkyl, and even more preferably, $R^2$ is a hydrogen atom, a halogen atom or methyl.

In the fused heterocyclic derivative represented by the formula (I) in the present invention, as another preferred embodiment, a compound which also has URAT1 inhibitory activity can be illustrated.

Effect of the Invention

The fused heterocyclic derivatives represented by the formula (I) of the present invention exert an excellent xanthine oxidase inhibitory activity and suppress the production of uric acid. Therefore, the fused heterocyclic derivatives represented by the formula (I) of the present invention or prodrugs thereof, or pharmaceutically acceptable salts thereof can extremely suppress the increase in serum uric acid level and are useful as an agent for the prevention or treatment of diseases associated with abnormal serum uric acid level such as hyperuricemia or the like.

MODE TO OPERATE THE INVENTION

The present invention is further illustrated in more detail by way of the following Reference Examples, Examples and Test Examples. However, the present invention is not limited thereto.

Reference Example 1

Ethyl 2-azido-3-(5-methylthiophen-2-yl)acrylate

To a solution of ethyl azidoacetate (10.6 g) in methanol (65 mL) was added sodium ethoxide (20% solution in ethanol, 27.2 g) under ice-cooling, and the mixture was stirred at the same temperature for 1 hour. 5-Methylthiophene-2-carbaldehyde (2.5 g) was added to this solution and the mixture was stirred at room temperature for 1 hour. To the reaction solution was added saturated ammonium chloride aqueous solution and water, and the resulting mixture was extracted with ethyl acetate. The organic layer was washed with brine, dried over anhydrous sodium sulfate, and concentrated under reduced pressure. The residue was purified by column chromatography on silica gel (eluent: n-hexane/ethyl acetate=100/0–90/10) to give the title compound (3.39 g)

Reference Example 2

Ethyl 2-methyl-4H-thieno[3,2-b]pyrrole-5-carboxylate

Ethyl 2-azido-3-(5-methylthiophen-2-yl)acrylate (3.38 g) was dissolved in m-xylene (30 mL) and the mixture was heated at reflux for 1 hour. The reaction solution was concentrated under reduced pressure. To the residue was added n-hexane and the residue was washed with n-hexane. The solid was collected by filtration, and dried under reduced pressure to give the title compound (2.56 g).

Reference Examples 3 and 4

The compounds of Reference Examples 3 and 4 were prepared in a similar manner to that described in Reference Example 2 using the corresponding starting materials.

Reference Example 5

Ethyl 6-bromo-2-methyl-4H-thieno[3,2-b]pyrrole-5-carboxylate

To a solution of ethyl 2-methyl-4H-thieno[3,2-b]pyrrole-5-carboxylate (1.0 g) in tetrahydrofuran (10 mL) was added N-Bromosuccinimide (0.94 g) under ice-cooling, and the mixture was stirred at the same temperature for 1 hour. To the reaction mixture was added water and the resulting mixture was extracted with ethyl acetate. The organic layer was concentrated under reduced pressure. The obtained residue was purified by column chromatography on silica gel (eluent: n-hexane/ethyl acetate=97/3–76/24) to give the title compound (0.96 g).

Reference Examples 6 and 7

The compounds of Reference Examples 6 and 7 were prepared in a similar manner to that described in Reference Example 5 using the corresponding starting materials.

Reference Example 8

Ethyl 6-cyano-2-methyl-4H-thieno[3,2-b]pyrrole-5-carboxylate

To a solution of ethyl 6-bromo-2-methyl-4H-thieno[3,2-b]pyrrole-5-carboxylate (0.96 g) in N-methylpyrrolidone (10 mL) were added zinc cyanide (1.17 g) and tetrakis(triphenylphosphine)palladium (0.38 g), and the mixture was stirred at 150° C. for 30 minutes using microwave reactor. To the reaction solution was added water and the resulting mixture was extracted with ethyl acetate. The organic layer was concentrated under reduced pressure. The obtained residue was purified by column chromatography on silica gel (eluent: n-hexane/ethyl acetate) to give the title compound (0.64 g).

Reference Examples 9 and 10

The compounds of Reference Examples 9 and 10 were prepared in a similar manner to that described in Reference Example 8 using the corresponding starting materials.

Reference Example 11

Ethyl 3-bromo-6-cyano-2-methyl-4H-thieno[3,2-b]pyrrole-5-carboxylate

Ethyl 6-cyano-2-methyl-4H-thieno[3,2-b]pyrrole-5-carboxylate (0.3 g), N-Bromosuccinimide (0.24 g) and acetic acid (2.5 mL) were dissolved in chloroform (5.0 mL) and the mixture was stirred at room temperature for 1 hour. To the reaction solution was added saturated sodium hydrogen carbonate aqueous solution. The organic layer was separated and concentrated under reduced pressure. The obtained residue was washed with diethyl ether, and dried under reduced pressure to give the title compound (0.20 g).

Reference Example 12

Ethyl 6-cyano-2,3-dimethyl-4H-thieno[3,2-b]pyrrole-5-carboxylate

To a solution of ethyl 3-bromo-6-cyano-2-methyl-4H-thieno[3,2-b]pyrrole-5-carboxylate (0.2 g) in 1,4-dioxane (4.0 mL) were added 2,4,6-trimethylboroxine (0.64 g), copper(I) iodide (50 mg), tripotassium phosphate (0.27 g) and tetrakis(triphenylphosphine)palladium (0.22 g), and the mixture was stirred at 150° C. for 150 minutes using microwave reactor. The reaction solution was concentrated under reduced pressure, and the obtained residue was purified by column chromatography on silica gel (eluent: n-hexane/ethyl acetate=76/24–55/45) to give the title compound (0.13 g).

Reference Example 13

6-Cyano-2-methyl-4H-thieno[3,2-b]pyrrole-5-carboxylic acid

To a mixed solution of ethyl 6-cyano-2-methyl-4H-thieno[3,2-b]pyrrole-5-carboxylate (0.64 g) in tetrahydrofuran (8.0 mL), ethanol (4.0 mL) and water (6.0 mL) was added lithium hydroxide monohydrate (1.14 g), and the mixture was stirred at 50° C. for 35 hours. The reaction solution was concentrated under reduced pressure. To the residue was added 2 mol/L hydrochloric acid (18 mL) and water. The precipitated solid was collected by filtration, washed with water, and dried under reduced pressure at 50° C. to give the title compound (0.59 g).

Reference Examples 14 to 16

The compounds of Reference Examples 14 to 16 were prepared in a similar manner to that described in Reference Example 13 using the corresponding starting materials.

Reference Example 17

6-Cyano-2-methyl-4H-thieno[3,2-b]pyrrole

To a solution of 6-cyano-2-methyl-4H-thieno[3,2-b]pyrrole-5-carboxylic acid (0.54 g) in quinoline (10 mL) was added Copper powder (33 mg), and the mixture was stirred at 200° C. for 30 minutes using microwave reactor. To the reaction solution was added water, and a precipitated insoluble matter was filtered through a Celite pad (registered trademark). The organic layer was separated and the aqueous layer was extracted with ethyl acetate. The combined organic layer was washed with 1 mol/L hydrochloric acid, water and brine, dried over anhydrous magnesium sulfate, and concentrated under reduced pressure. The obtained residue was purified by column chromatography on silica gel (eluent: n-hexane/ethyl acetate=76/24–53/47) to give the title compound (0.37 g).

Reference Examples 18 to 20

The compounds of Reference Examples 18 to 20 were prepared in a similar manner to that described in Reference Example 17 using the corresponding starting materials.

Reference Example 21

Methyl 4-(6-cyano-2-methyl-thieno[3,2-b]pyrrol-4-yl)-2-(methoxymethoxy)benzoate

To a solution of 6-cyano-2-methyl-4H-thieno[3,2-b]pyrrole (0.37 g) in toluene (10 mL) were added methyl 4-iodo-2-(methoxymethoxy)benzoate (0.73 g), copper(I) iodide (43 mg), trans-N,N'-dimethylcyclohexanediamine (65 mg) and potassium carbonate (0.66 g), and the mixture was stirred at 170° C. for 20 minutes using microwave reactor. The reaction solution was concentrated under reduced pressure, and the residue was purified by column chromatography on silica gel (eluent: n-hexane/ethyl acetate=78/22–57/43) to give the title compound (0.63 g).

Reference Examples 22 to 24

The compounds of Reference Examples 22 to 24 were prepared in a similar manner to that described in Reference Examples 21 using the corresponding starting materials.

Reference Example 25

(3-Bromothiophen-2-yl)-acetonitrile

3-Bromo-2-(bromomethyl)thiophene (7.1 g) and potassium cyanide (2.7 g) were dissolved in ethanol (93 mL) and water (17 mL), and the mixture was stirred at 50° C. for 2 hours. The reaction solution was concentrated under reduced pressure, and to the residue was added water. The resulting mixture was extracted with ethyl acetate. The organic layer was washed with brine, dried over anhydrous magnesium sulfate, and concentrated under reduced pressure. The obtained residue was purified by column chromatography on silica gel (eluent: n-hexane/ethyl acetate=100/0–80/20) to give the title compound (4.0 g).

Example 1

4-(6-Cyano-2-methyl-thieno[3,2-b]pyrrol-4-yl)-2-hydroxybenzoic acid

To a mixed solution of methyl 4-(6-cyano-2-methyl-thieno[3,2-b]pyrrol-4-yl)-2-(methoxymethoxy)benzoate (0.63 g) in tetrahydrofuran (10 mL), ethanol (5.0 mL) and water (5.0 mL) was added lithium hydroxide monohydrate (0.22 g), and the mixture was stirred at room temperature for 4 hours. Then 1 mol/L hydrochloric acid (10.6 mL) was added to the reaction solution and the resulting mixture was stirred at 50° C. for 5 hours. The reaction solution was concentrated under reduced pressure. To the residue was added water. The precipitated solid was collected by filtration, washed with water, and dried under reduced pressure at 50° C. to give the title compound (0.52 g).

Examples 2 to 4

The compounds of Examples 2 to 4 were prepared in a similar manner to that described in Example 1 using the corresponding starting materials.

Example 5

4-(6-Cyano-thieno[3,2-b]pyrrol-4-yl)-2-hydroxybenzoic acid

To a solution of 2-(3-bromothiophen-2-yl)acetonitrile (1.0 g) and ethyl formate (3.7 g) in dimethyl sulfoxide (5.0 mL)

was added sodium ethoxide (20% solution in ethanol, 3.1 mL), and the mixture was stirred at room temperature for 3 hours. 2.5 mol/L hydrochloric acid ethanol solution (3.6 mL) and 4-amino-2-hydroxybenzoic acid (0.9 g) were added to reaction solution. The mixture was stirred at 50° C. for 5 hours. To the reaction solution was added water. The precipitated solid was collected by filtration, washed with water, and dried under reduced pressure at 50° C. for 3 hours. The obtained residue was purified by column chromatography on silica gel (eluent: dichloromethane/methanol=87/13–78/22) to give the condensate (0.91 g). To a solution of this condensate (0.91 g) in dimethyl sulfoxide (4.5 mL) were added copper(I) iodide (47 mg), ethylene glycol (0.3 g) and tripotassium phosphate (1.1 g), and the mixture was stirred at 80° C. for 5 hours. After cooling to 50° C., to the mixture was added 2 mol/L hydrochloric acid (8.7 mL) and the mixture was stirred at room temperature for 1 hour. The precipitated solid was collected by filtration, washed with mixed solution of water and dimethyl sulfoxide, 1 mol/L hydrochloric acid and water, and dried under reduced pressure at 50° C. to give the title compound (0.45 g).

Examples 6 to 9

The compounds of Examples 6 to 9 were prepared in a similar manner to that described in Example 5 using the corresponding starting materials.

Tables 1 to 4 show the chemical structures and $^1$H-NMR data of the above compounds of Reference Examples 1 to 25 and Examples 1 to 9.

The abbreviations in these Tables: "Ref No.", "Ex No.", "Strc", "Solv", "Et", "Me" and "MOMO" represent Reference Example number, Example number, chemical structure, measurement solvent of $^1$H-NMR, an ethyl group, a methyl group and a methoxymethoxy group, respectively.

TABLE 1

| Ref. No. | Strc. | $^1$H-NMR (CDCl$_3$) δ ppm: |
|---|---|---|
| 1 | [structure] | 1.38 (3H, t, J = 7.0 Hz), 2.50-2.55 (3H, m), 4.33 (2H, q, J = 7.0 Hz), 6.70-6.75 (1H, m), 7.05-7.15 (2H, m) |
| 2 | [structure] | 1.38 (3H, t, J = 7.1 Hz), 2.50-2.60 (3H, m), 4.35 (2H, q, J = 7.1 Hz), 6.60-6.70 (1H, m), 7.00-7.10 (1H, m), 9.05 (1H, brs) |
| 3 | [structure] | 1.38 (3H, t, J = 7.4 Hz), 2.45-2.55 (3H, m), 4.35 (2H, q, J = 7.4 Hz), 6.60-6.70 (1H, m), 6.90-7.00 (1H, m), 9.35 (1H, brs) |
| 4 | [structure] | 1.34 (3H, t, J = 7.7 Hz), 1.38 (3H, t, J = 7.2 Hz), 2.80-2.95 (2H, m), 4.35 (2H, q, J = 7.2 Hz), 6.60-6.70 (1H, m), 7.00-7.10 (1H, m), 8.98 (1H, brs) |
| 5 | [structure] | 1.41 (3H, t, J = 6.9 Hz), 2.50-2.60 (3H, m), 4.39 (2H, q, J = 6.9 Hz), 6.60-6.70 (1H, m), 9.14 (1H, brs) |

TABLE 1-continued

| Ref. No. | Strc. | $^1$H-NMR (CDCl$_3$) δ ppm: |
|---|---|---|
| 6 | [structure] | 1.41 (3H, t, J = 7.3 Hz), 2.45-2.55 (3H, m), 4.39 (2H, q, J = 7.3 Hz), 6.60-6.65 (1H, m), 9.34 (1H, brs) |
| 7 | [structure] | 1.34 (3H, t, J = 7.4 Hz), 1.41 (3H, t, J = 7.1 Hz), 2.80-2.95 (2H, m), 4.39 (2H, q, J = 7.1 Hz), 6.65-6.75 (1H, m), 9.15 (1H, brs) |
| 8 | [structure] | 1.45 (3H, t, J = 7.2 Hz), 2.55-2.65 (3H, m), 4.46 (2H, q, J = 7.2 Hz), 6.65-6.75 (1H, m), 9.43 (1H, brs) |
| 9 | [structure] | 1.46 (3H, t, J = 6.8 Hz), 2.50-2.60 (3H, m), 4.47 (2H, q, J = 6.8 Hz), 6.75-6.85 (1H, m), 9.87 (1H, brs) |

TABLE 2

| Ref. No. | Strc. | (Solv.) $^1$H-NMR δ ppm: |
|---|---|---|
| 10 | [structure] | (CDCl$_3$) 1.36 (3H, t, J = 7.6 Hz), 1.46 (3H, t, J = 7.1 Hz), 2.85-3.00 (2H, m), 4.47 (2H, q, J = 7.1 Hz), 6.65-6.75 (1H, m), 9.56 (1H, brs) |
| 11 | [structure] | (CDCl$_3$) 1.47 (3H, t, J = 7.2 Hz), 2.51 (3H, s), 4.49 (2H, q, J = 7.2 Hz), 9.46 (1H, brs) |
| 12 | [structure] | (CDCl$_3$) 1.46 (3H, t, J = 7.0 Hz), 2.20-2.25 (3H, m), 2.40-2.50 (3H, m), 4.47 (2H, q, J = 7.0 Hz), 9.60 (1H, brs) |
| 13 | [structure] | (DMSO-d6) 2.50-2.60 (3H, m), 6.85-6.90 (1H, m), 12.90 (1H, s), 13.70 (1H, brs) |
| 14 | [structure] | (DMSO-d6) 2.45-2.55 (3H, m), 6.85-6.95 (1H, m), 13.12 (1H, s), 13.65 (1H, brs) |

TABLE 2-continued

| Ref. No. | Strc. | (Solv.) $^1$H-NMR δ ppm: |
|---|---|---|
| 15 | 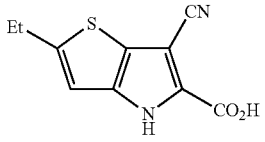 | (DMSO-d6) 1.27 (3H, t, J = 7.4 Hz), 2.80-2.95 (2H, m), 6.80-6.90 (1H, m), 13.00 (1H, s), 13.70 (1H, brs) |
| 16 | 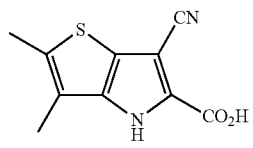 | (DMSO-d6) 2.22 (3H, s), 2.40 (3H, s), 13.10 (1H, s), 13.70 (1H, brs) |
| 17 | 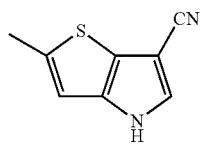 | (CDCl$_3$) 2.50-2.60 (3H, m), 6.65-6.75 (1H, m), 7.35-7.45 (1H, m), 8.69 (1H, brs) |
| 18 |  | (CDCl$_3$) 2.50-2.55 (3H, m), 6.75-6.80 (1H, m), 7.40-7.50 (1H, m), 8.75 (1H, brs) |

TABLE 3

| Ref. No. | Strc. | $^1$H-NMR (CDCl$_3$) δ ppm: |
|---|---|---|
| 19 | 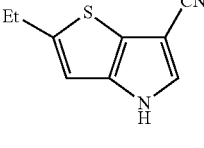 | 1.34 (3H, t, J = 8.0 Hz), 2.80-2.95 (2H, m), 6.65-6.75 (1H, m), 7.35-7.45 (1H, m), 8.73 (1H, brs) |
| 20 | 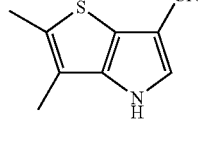 | 2.15-2.25 (3H, m), 2.35-2.45 (3H, m), 7.35-7.45 (1H, m), 8.47 (1H, brs) |
| 21 | 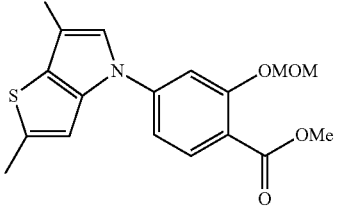 | 2.55-2.65 (3H, m), 3.56 (3H, s), 3.93 (3H, s), 5.33 (2H, s), 6.80-6.90 (1H, m), 7.10-7.20 (1H, m), 7.30-7.40 (1H, m), 7.55-7.65 (1H, m), 7.90-8.00 (1H, m) |
| 22 | 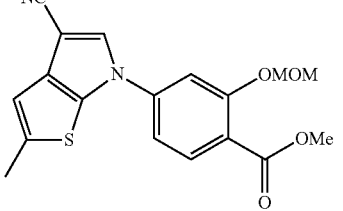 | 2.50-2.60 (3H, m), 3.57 (3H, s), 3.93 (3H, s), 5.35 (2H, s), 6.80-6.90 (1H, m), 7.15-7.25 (1H, m), 7.40-7.50 (1H, m), 7.65-7.75 (1H, m), 7.90-8.05 (1H, m) |

TABLE 3-continued

| Ref. No. | Strc. | $^1$H-NMR (CDCl$_3$) δ ppm: |
|---|---|---|
| 23 | 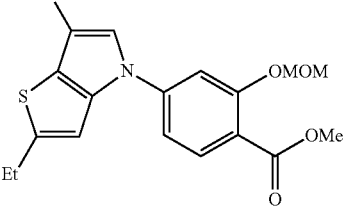 | 1.35 (3H, t, J = 8.0 Hz), 2.85-3.00 (2H, m), 3.56 (3H, s), 3.93 (3H, s), 5.33 (2H, s), 6.85-6.90 (1H, m), 7.10-7.20 (1H, m), 7.35-7.40 (1H, m), 7.55-7.65 (1H, m), 7.90-8.00 (1H, m) |
| 24 | 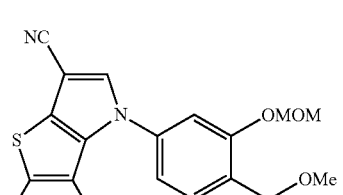 | 1.85-1.95 (3H, m), 2.35-2.45 (3H, m), 3.53 (3H, s), 3.94 (3H, s), 5.29 (2H, s), 7.00-7.10 (1H, m), 7.20-7.30 (1H, m), 7.35-7.40 (1H, m), 7.90-7.95 (1H, m) |
| 25 | 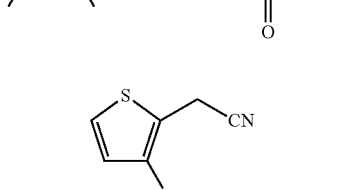 | 3.07 (2H, s), 6.95-7.05 (1H, m), 7.25-7.35 (1H, m) |

TABLE 4

| Ex. No. | Strc. | $^1$H-NMR (DMSO-d6) δ ppm: |
|---|---|---|
| 1 | 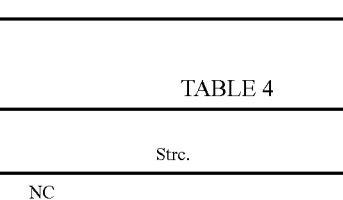 | 2.50-2.60 (3H, m), 7.20-7.30 (3H, m), 7.90-8.00 (1H, m), 8.40-8.50 (1H, m), 11.76 (1H, brs) |
| 2 | 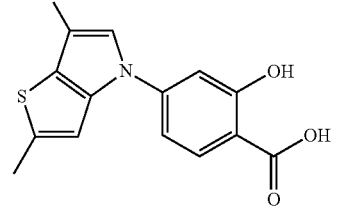 | 2.50-2.60 (3H, m), 6.95-7.05 (1H, m), 7.20-7.30 (2H, m), 7.95-8.05 (1H, m), 8.55-8.65 (1H, m), 11.76 (1H, brs) |
| 3 | 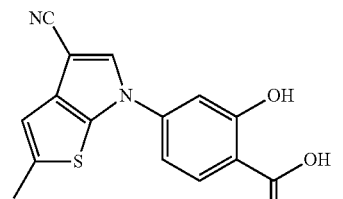 | 1.29 (3H, t, J = 7.5 Hz), 2.80-3.00 (2H, m), 7.20-7.35 (3H, m), 7.90-8.00 (1H, m), 8.40-8.50 (1H, m), 11.76 (1H, brs) |

TABLE 4-continued

| Ex. No. | Strc. | $^1$H-NMR (DMSO-d6) δ ppm: |
|---|---|---|
| 4 | (structure: 2,3-dimethyl-5-cyano-thieno-pyrrole N-linked to 3-hydroxy-4-carboxyphenyl) | 1.89 (3H, s), 2.39 (3H, s), 7.00-7.20 (2H, m), 7.85-8.15 (2H, m), 11.75 (1H, brs) |
| 5 | (structure: cyano-thieno[3,2-b]pyrrole N-linked to 3-hydroxy-4-carboxyphenyl) | 7.25-7.35 (2H, m), 7.40-7.50 (1H, m), 7.65-7.75 (1H, m), 7.90-8.00 (1H, m), 8.50-8.60 (1H, m), 11.69 (1H, brs) |
| 6 | (structure: cyano-furo-pyrrole N-linked to 3-hydroxy-4-carboxyphenyl) | 7.15-7.35 (3H, m), 7.85-8.00 (2H, m), 8.45-8.55 (1H, m) |
| 7 | (structure: cyano-thieno-pyrrole isomer N-linked to 3-hydroxy-4-carboxyphenyl) | 7.30 (1H, d, J = 2.3 Hz), 7.34 (1H, dd, J = 8.7 Hz, 2.3 Hz), 7.64 (1H, d, J = 2.6 Hz), 7.72 (1H, d, J = 2.6 Hz), 7.94 (1H, d, J = 8.6 Hz), 8.97 (1H, s) |
| 8 | (structure: 2-bromo-cyano-thieno-pyrrole N-linked to 3-hydroxy-4-carboxyphenyl) | 7.00-7.30 (2H, m), 7.62 (1H, s), 7.85-8.05 (1H, m), 8.73 (1H, s) |
| 9 | (structure: cyano-thieno-pyrrole N-linked to 3-hydroxy-4-carboxyphenyl) | 7.10-7.25 (3H, m), 7.29 (1H, d, J = 5.5 Hz), 7.45-7.50 (1H, m), 7.65-7.70 (1H, m) |

Test Example 1

Xanthine Oxidase Inhibitory Activity (1) Preparation of Test Compounds

Test compounds were dissolved in dimethyl sulfoxide (DMSO) (manufactured by Wako pure chemical) at 40 mM concentration and then diluted to intended concentrations with phosphate-buffered saline (PBS).

(2) Method for Measurement

Xanthine oxidase (from bovine milk, Sigma) was prepared with phosphate-buffered saline (PBS) at 0.02 units/mL, and then the solution was added to 96 well plates at 50 μL/well. In addition, test compounds diluted with PBS were added at 50 μL/well. Xanthine (manufactured by Wako pure chemical) at 200 μM prepared with PBS was added at 100 μL/well, and the reaction was conducted for 10 minutes at room temperature. Absorbance at 290 nm was measured by using a microplate reader SpectraMax Plus 384 (manufactured by Molecular device). The absorbance under a condition without xanthine is 0%, and control without test compounds is 100%. Fifty % inhibitory concentration of a test compounds ($IC_{50}$) was calculated (Table 5). "Ex. No." in the table indicates Example number.

TABLE 5

| Ex. No. | $IC_{50}$ (nM) |
|---|---|
| 1 | 13 |
| 5 | 10 |
| 7 | 10 |
| 8 | 14 |
| 9 | 13 |

Test Example 2

Inhibitory Activity of Uric Acid Transport with Human URAT1 Expressing Cells (1) Cells Used in the Test URAT1-expressing HEK293 cells (HEK293 cells transfected with vector containing human URAT1 cDNA) and control cells (HEK293 cells transfected with vector alone) were used.

URAT1-expressing cells and control cells were seeded in collagen I-coated 24-well plates (manufactured by Becton, Dickinson and Company) at 1 to $4 \times 10^5$ cells/well, and cultured in $CO_2$ incubator (37° C., $CO_2$: 5%) for 1 to 3 days, and then the following measurement of uric acid transport was conducted. In addition, Dulbecco's Modified Eagle Medium (manufactured by Invitrogen) containing 9% fetal bovine serum (manufactured by Invitrogen), antibiotic-antimycotic (manufactured by Invitrogen) and 2 mmol/L L-glutamine were used for the culture.

(2) Preparation of Test Compounds $^{14}$C-labeled uric acid ($^{14}$C uric acid) (manufactured by American Radiolabeled Chemicals, Inc.) was dissolved in Hanks' balanced salt solution (HBSS) (manufactured by Invitrogen) to prepare HBSS containing $^{14}$C uric acid at 50 μM. Test compounds were dissolved in DMSO and then diluted to 1000-fold with the prepared HBSS containing $^{14}$C uric acid above to prepare $^{14}$C uric acid solution containing the indicated concentration of test compounds (final concentration of DMSO: 0.1%). $^{14}$C uric acid solution containing 0.1% DMSO was prepared as a control.

(3) Measurement of Uric Acid Transport

After the medium was removed from the plates in which cells were seeded, and 1 mL of HBSS was added to the cells. After the HBSS was removed, 0.3 mL of HBSS was newly added to the cells, which were incubated at 37° C. for 15 minutes. After the HBSS was removed, 0.3 mL of $^{14}$C uric acid solution containing 0.1% DMSO or test compounds was added to the cells, which were then incubated at 37° C. for 2 minutes. After the incubation, the solution was removed, and the cells were washed once with 1 mL of ice-cold phosphate-buffered saline containing 0.2% BSA, and washed twice with 1 mL of ice-cold PBS. After the PBS was removed, the cells were lysed by addition of 0.5 mL of 0.1 mol/L NaOH aqueous solution for each well. The cell lysates (0.3 mL/well) were transferred into glass vials, and mixed with 10 mL of a scintillator (Hionic-Fluor, manufactured by Perkin Elmer). The radioactivity was measured by means of a liquid scintillation counter.

(4) Protein Determination

Protein concentration in the cell lysates was determined by BCA Protein Assay Kit (manufactured by Pierce) and then amount of protein (mg/well) was calculated.

(5) Calculation of the Percent Inhibition of Uric Acid Uptake for Each Compound

Uric acid uptake activity in each well was calculated by the following formula.

Uric acid uptake activity (p mol/mg protein)=radioactivity (dpm/well)/[amount of protein (mg/well)×concentration of radioactivity in HBSS containing $^{14}$C uric acid (dpm/p mol)]

Percent inhibition was calculated according to the following formula.

Percent inhibition (%)=[1−(B−C)/(A−C)]×100

A: Uric acid uptake activity in URAT1-expressing HEK293 cells in the presence of 0.1% DMSO B: Uric acid uptake activity in URAT1-expressing HEK293 cells in the presence of test compounds C: Uric acid uptake activity in control cells in the presence of 0.1% DMSO (6) Result The compound of Example 9 showed not less than 50% inhibition in a concentration of 10 μM.

INDUSTRIAL APPLICABILITY

The fused heterocyclic derivatives represented by the formula (I) of the present invention, or prodrugs thereof, or pharmaceutically acceptable salts thereof exert an excellent xanthine oxidase inhibitory activity, and therefore, can exert an inhibitory activity of uric acid production and lower the serum uric acid level. Therefore, the present invention can provide an agent for the prevention or treatment of hyperuricemia, gouty tophus, gouty arthritis, renal disorder associated with hyperuricemia, urinary calculi or the like.

The invention claimed is:

1. A fused heterocyclic derivative represented by the formula (I):

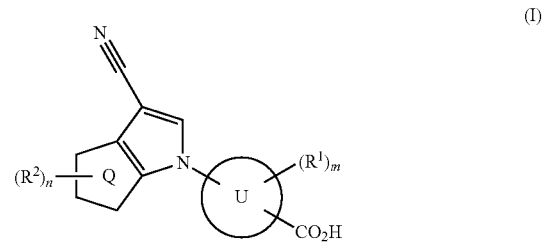

wherein ring U represents a $C_{6-10}$ aryl ring or a 5 or 6-membered heteroaryl ring;

m represents an integral number from 1 to 2, and when m is 2, two $R^1$ are optionally the same or different from each other;

$R^1$ represents a hydrogen atom, a halogen atom, a hydroxy group, amino, or $C_{1-6}$ alkyl which may have a fluorine atom;

ring Q represents a 5-membered heteroaryl ring;

n represents an integral number from 1 to 3, and when n is 2 or 3, these $R^2$ are optionally the same or different from each other;

$R^2$ represents any of the following (1) to (8):
(1) a hydrogen atom;
(2) a halogen atom;
(3) a hydroxy group;
(4) amino;
(5) cyano;
(6) carboxy;
(7) carbamoyl;
(8) $C_{1-6}$ alkyl, $C_{2-6}$ alkenyl, $C_{2-6}$ alkynyl, $C_{1-6}$ alkoxy, mono or di-$C_{1-6}$ alkylamino, $C_{2-7}$ acyl, $C_{1-6}$ alkoxycarbonyl, $C_{2-7}$ acylamino, $C_{2-7}$ acyl($C_{1-6}$ alkyl)amino, mono or di-$C_{1-6}$ alkylcarbamoyl, $C_{1-6}$ alkylsulfonyl, $C_{1-6}$ alkylsulfonylamino, $C_{1-6}$ alkylsulfonyl($C_{1-6}$ alkyl)amino, mono or di-$C_{1-6}$ alkylsulfamoyl, $C_{1-6}$ alkylthio, $C_{3-8}$ cycloalkyl, 3 to 8-membered heterocycloalkyl, $C_{5-8}$ cycloalkenyl, 5 to 8-membered heterocycloalkenyl, $C_{3-8}$ cycloalkyloxy, $C_{3-8}$ cycloalkyl $C_{1-6}$ alkoxy, mono or di-$C_{3-8}$ cycloalkylamino, $C_{3-8}$ cycloalkyl($C_{1-6}$ alkyl)amino, $C_{6-10}$ aryl, 5 or 6-membered heteroaryl, $C_{6-10}$ aryloxy, $C_{6-10}$ aryl $C_{1-6}$ alkoxy, $C_{6-10}$ arylamino, $C_{6-10}$ aryl($C_{1-6}$ alkyl)amino, $C_{6-10}$ arylcarbonyl, $C_{6-10}$ arylcarbonylamino, $C_{6-10}$ arylcarbonyl($C_{1-6}$ alkyl)amino, 5 or 6-membered heteroaryloxy, 5 or 6-membered heteroaryl $C_{1-6}$ alkoxy, 5 or 6-membered heteroarylamino or 5 or 6-membered heteroaryl($C_{1-6}$ alkyl)amino each of which may independently have any group selected from substituent group A; and substituent group A is selected from the group consisting of a fluorine atom, a chlorine atom, a hydroxy group, amino, carboxy, carbamoyl, cyano, $C_{1-6}$ alkyl, $C_{1-6}$ alkoxy and mono or di-$C_{1-6}$ alkylamino; or a prodrug thereof, or a pharmaceutically acceptable salt thereof.

2. A fused heterocyclic derivative as claimed in claim 1, wherein ring Q represents a furan ring, a pyrrole ring or a thiophene ring, or a prodrug thereof, or a pharmaceutically acceptable salt thereof.

3. A fused heterocyclic derivative as claimed in claim 2, wherein the fused heterocyclic derivative represented by the formula (I) is any one of the compounds represented by the formula (Ia) to (Ic):

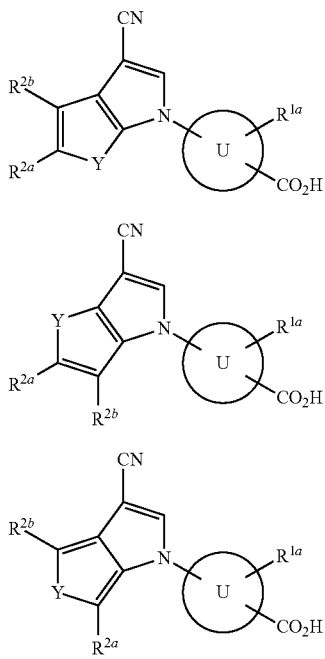

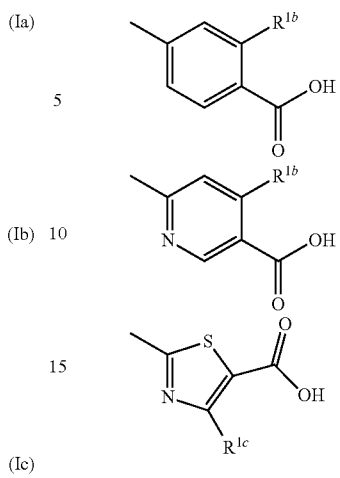

(Ia)

(Ib)

(Ic)

wherein
R$^{1b}$ represents a hydrogen atom or a hydroxy group; and
R$^{1c}$ represents a hydrogen atom or methyl; or a prodrug thereof, or a pharmaceutically acceptable salt thereof.

7. A fused heterocyclic derivative as claimed in claim 6, wherein the group represented by the formula:

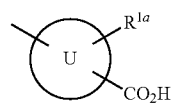

is a group represented by the formula:

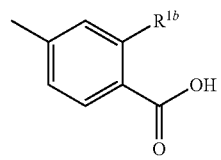

in the formula, R$^{1b}$ has the same meaning as described in claim 6, or a prodrug thereof, or a pharmaceutically acceptable salt thereof.

8. A fused heterocyclic derivative as claimed in claim 3, wherein R$^{2a}$ and R$^{2b}$ independently represent any of the following (b1) to (b3):
  (b1) a hydrogen atom;
  (b2) a halogen atom;
  (b3) C$_{1-6}$ alkyl, C$_{1-6}$ alkoxy, mono or di-C$_{1-6}$ alkylamino, C$_{1-6}$ alkoxycarbonyl, mono or di-C$_{1-6}$ alkylcarbamoyl, C$_{3-8}$ cycloalkyl, 3 to 8-membered heterocycloalkyl, C$_{6-10}$ aryl or 5 or 6-membered heteroaryl each of which may have a fluorine atom; or a prodrug thereof, or a pharmaceutically acceptable salt thereof.

9. A fused heterocyclic derivative as claimed in claim 8, wherein R$^{2a}$ and R$^{2b}$ independently represent a hydrogen atom, a halogen atom or C$_{1-6}$ alkyl which may have a fluorine atom, or a prodrug thereof, or a pharmaceutically acceptable salt thereof.

10. A fused heterocyclic derivative as claimed in claim 9, wherein R$^{1a}$ represents a hydroxy group; and
  R$^{2a}$ and R$^{2b}$ independently represent a hydrogen atom or methyl, or a prodrug thereof, or a pharmaceutically acceptable salt thereof.

wherein
Y represents a sulfur atom or an oxygen atom;
R$^{1a}$ represents a hydrogen atom, a fluorine atom, a hydroxy group or C$_{1-6}$ alkyl;
R$^{2a}$ and R$^{2b}$ independently represent any of the following (a1) to (a3):
  (a1) a hydrogen atom;
  (a2) a halogen atom;
  (a3) C$_{1-6}$ alkyl, C$_{1-6}$ alkoxy, mono or di-C$_{16}$ alkylamino, C$_{2-7}$ acyl, C$_{1-6}$ alkoxycarbonyl, mono or di-C$_{1-6}$ alkylcarbamoyl, C$_{3-8}$ cycloalkyl, 3 to 8-membered heterocycloalkyl, C$_{3-8}$ cycloalkyloxy, mono or di-C$_{3-8}$ cycloalkylamino, C$_{6-10}$ aryl or 5 or 6-membered heteroaryl each of which may have any group selected from substituent group A; and
ring U and substituent group A have the same meanings as described in claim 1, or a prodrug thereof, or a pharmaceutically acceptable salt thereof.

4. A fused heterocyclic derivative as claimed in claim 3, wherein Y represents a sulfur atom, or a prodrug thereof, or a pharmaceutically acceptable salt thereof.

5. A fused heterocyclic derivative as claimed in claim 1, wherein ring U represents a benzene ring, a pyridine ring or a thiazole ring, or a prodrug thereof, or a pharmaceutically acceptable salt thereof.

6. A fused heterocyclic derivative as claimed in claim 5, wherein the group represented by the formula:

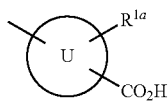

is a group represented by any of the formulas:

11. A pharmaceutical composition comprising as an active ingredient a fused heterocyclic derivative as claimed in claim 1, or a prodrug thereof, or a pharmaceutically acceptable salt thereof and at least a pharmaceutical additive.

12. A xanthine oxidase inhibitor comprising as an active ingredient a fused heterocyclic derivative as claimed in claim 1, or a prodrug thereof, or a pharmaceutically acceptable salt thereof.

* * * * *